(12) United States Patent
Krauss et al.

(10) Patent No.: US 6,726,904 B2
(45) Date of Patent: Apr. 27, 2004

(54) METHOD FOR TRANSMITTING ACOUSTIC WAVES

(75) Inventors: Werner Krauss, Knittlingen (DE); Peter Jaggy, Ötisheim (DE); Edgar Bauer, Kraichtal (DE); Hermann Benkhoff, Duderstadt (DE)

(73) Assignees: Richard Wolf GmbH, Knittlingen (DE); TachnoGel GmbH & Co. KG, Duderstadt (DE)

( * ) Notice: Subject to any disclaimer, the term of this patent is extended or adjusted under 35 U.S.C. 154(b) by 0 days.

(21) Appl. No.: 09/974,112

(22) Filed: Oct. 9, 2001

(65) Prior Publication Data

US 2002/0045849 A1 Apr. 18, 2002

(30) Foreign Application Priority Data

Oct. 9, 2000 (DE) .......................................... 100 50 114

(51) Int. Cl.$^7$ .......................... A61K 31/74; A61K 47/48
(52) U.S. Cl. ................. 424/78.17; 424/78.08; 424/437
(58) Field of Search ........................... 424/78.08, 78.17, 424/422, 437

(56) References Cited

U.S. PATENT DOCUMENTS 5,420,170 A * 5/1995 Lutter et al. ................. 521/164
6,420,447 B1 * 7/2002 Kittel et al. ................. 521/174

FOREIGN PATENT DOCUMENTS

| DE | 33 12014 A1 | 10/1984 |
|----|-------------|---------|
| DE | 689 27 722 T2 | 6/1997 |
| DE | 195 09 004 C1 | 10/1998 |
| EP | 0 511 570 B1 | 3/1997 |
| JP | 55-063636 A | 11/1978 |

* cited by examiner

Primary Examiner—Thurman K. Page
Assistant Examiner—Liliana Di Nola-Baron
(74) Attorney, Agent, or Firm—Akin Gump Strauss Hauer & Feld, L.L.P.

(57) ABSTRACT

The invention relates to the use of a gel mass based on reaction products of polyols and polyisocyanates, wherein the polyol component consists of one or more polyols with hydroxyl numbers below 112 and where appropriate other polyols and additives known from polyol chemistry, the isocyanate number of the reaction mixture lies in the range of 15 to 59.81 and the product of the isocyanate functionality and the functionality of the polyol components is at least 6.15, as a coupling medium for transmitting acoustic waves from a sound source onto the body of the patient.

18 Claims, 1 Drawing Sheet

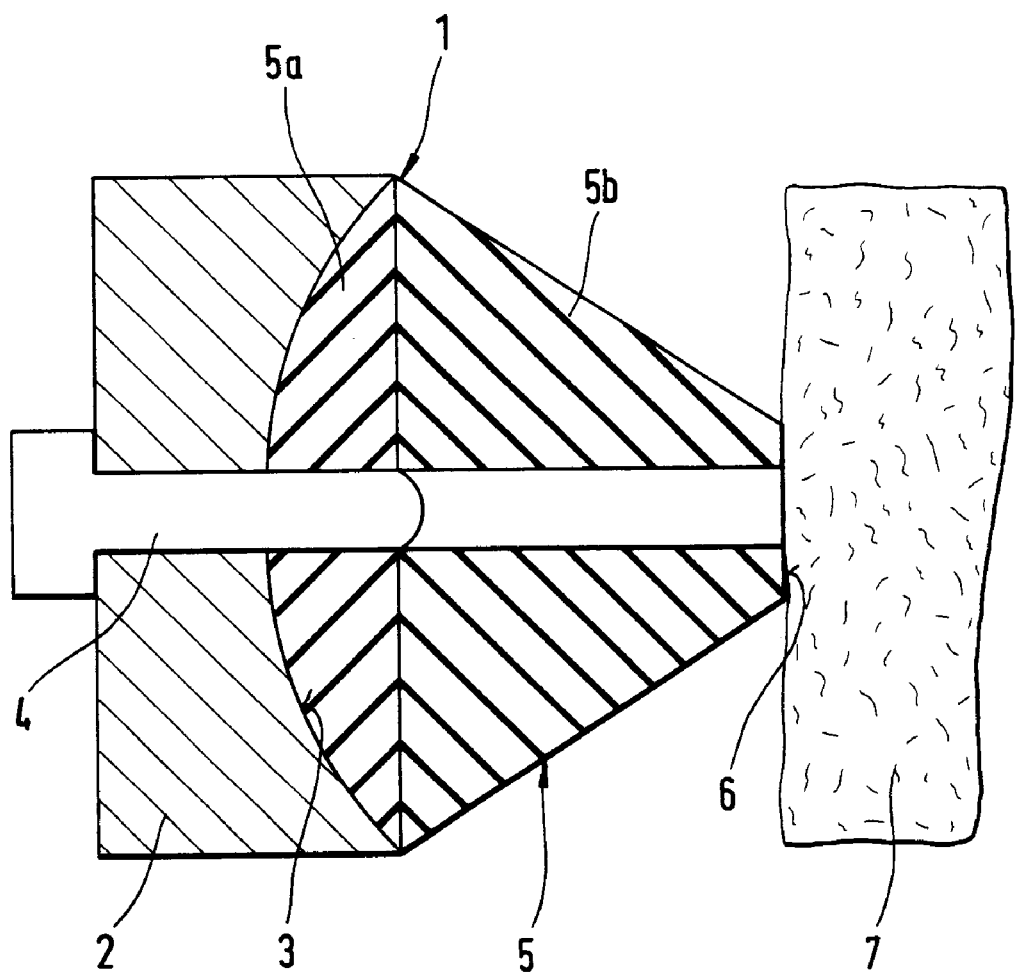

METHOD FOR TRANSMITTING ACOUSTIC WAVES

BACKGROUND OF THE INVENTION

The invention relates to the use of a gel mass as a coupling medium for transmitting acoustic waves from a sound source onto the body of a patient.

Lithotripsy and hyperthermia apparatus are generally known as acoustic therapy apparatus. These apparatus have an electro-acoustic transducer as a source of focused acoustic waves, which are emitted from the transducer irradiation surface, and a coupling cushion mounted in front of the irradiation surface provided with an inner coupling surface lying against the irradiation surface and an outer coupling surface for application on the patient. It is also possible to simultaneously work with two or more coupling cushions arranged in layers when one, for example, wishes to reduce the penetration depth of the transducer focus in the body of the patient in comparison to the penetration depth which is achieved with the application of only one coupling cushion. Moreover, in the case of lithotripsy there are produced focused shock waves. With hyperthermia, ultrasound waves in the form of permanent sound or sound pulses are used.

German Patent DE 195 09 004 C1suggests a therapy apparatus which may be equipped with various coupling cushions which are held available. The coupling cushions may in each case be exchangeably connected to the transducer in that, for example, with their coupling surface they are laid into a transducer shell and fastened on the transducer in a suitable manner.

Coupling cushions are required in order to bridge the distance between the irradiation surface of the transducer and the body surface of the patient as a so-called forward path which optionally may be enlarged and variably adjusted by use of several coupling cushions (DE 33 12 014 A1).

It is known to design coupling cushions of certain acoustic coupling media, such as polyacrylamide gel or synthetic rubber, as a shaped body or to fill a cushion casing with such a gel (DE 195 09 004). However, it has been shown that such materials or coupling media bring with them relatively large sound energy losses and also are unsatisfactory with regard to the desired high sound absorption with the transition from the transducer irradiation surface to the coupling medium. Furthermore, it has been ascertained that known gels may lead to irritations of the skin of the patient when they are brought into direct contact with this. Finally, it has been ascertained that the gels common until now are often not softener-free and are not sufficiently UV-stable, so that in the course of time there may occur a disadvantageous change of the acoustic properties of this coupling medium.

BRIEF SUMMARY OF THE INVENTION

It is therefore the object of the invention to suggest a coupling medium which is distinguished by low sound energy losses, guarantees a high sound absorption with the transition of the ultrasound from the transducer irradiation surface, and offers a low acoustic resistance. Further demands on the coupling medium are that it be friendly to the skin, have a good shape stability, and, for the above mentioned reasons, be softener-free and UV-stable.

For achieving this object as a coupling medium for transmitting acoustic waves from a sound source onto the body of a patient, there is used a gel mass based on the reaction products of polyols and polyisocyanates, wherein the polyol component consists of one or more polyols with hydroxyl numbers below 112 and where appropriate other polyols and additives known from polyol chemistry, the isocyanate number of the reaction mixture lies in the range of 15 to 59.81, and the product of the isocyanate functionality and the functionality of the polyol components is at least 6.15.

Usefully, the gel mass additionally contains fillers and/or additives in a total quantity of up to 50% by weight with respect to the total weight of the gel mass.

The isocyanate number is to be understood as the equivalent ratio (NCO/OH)×100. Thus, for example, an isocyanate number of 15 means that for one reactive OH group in the polyols there are present 0.15 reactive NCO groups in the polyisocyanate or for one reactive NCO group in the polyisocyanate there are present 6.67 reactive OH groups in the polyols. Accordingly, an isocyanate number of 70 means that for one reactive OH group in the polyols there are present 0.7 reactive NCO groups in the polyisocyanate or for one reactive NCO group in the polyisocyanate there are present 1.43 reactive OH groups in the polyols.

Further details for manufacturing the gel mass suggested for use according to the invention are to be found in EP 0 511 570 B1, from which such a gel mass is known, and specifically for use in pressure-distributing elements in the form of seat cushions and rests for body surfaces.

BRIEF DESCRIPTION OF THE SEVERAL VIEWS OF THE DRAWING

In the drawing there is shown one embodiment of the invention. The single FIGURE shows schematically and greatly simplified a section through an acoustic therapy apparatus in the region of its electroacoustic transducer with a coupling cushion.

DETAILED DESCRIPTION OF THE INVENTION

The therapy apparatus 1 comprises a transducer 2 as a source for acoustic waves, as for example shock waves with lithotripsy. The transducer 2 has a concavely formed irradiation surface 3, whose shape is given in known manner such that the transducer consists of a carrier in the shape of a circular segment in which piezoelectric transducer elements are mosaically arranged, which are activated by a supply unit in a pulsed manner with a high voltage.

The apparatus 1, apart from being equipped with the therapy transducer 2, is also equipped with a diagnosis transducer 4, which is designed as a B-scanner and via which, in the form of sectioned pictures, the object to be irradiated and its position in relation to the transducer focus may be imaged on a monitor.

The transmission of the acoustic therapy waves onto the tissue of the patient 7 is effected by way of a coupling cushion 5. This lies on the skin of the patient with its outer coupling surface 6. The coupling cushion may consist of one piece as a shape-stable body from the gel suggested as a coupling medium. With the shown embodiment, however, a single-part coupling cushion alone is not used. Rather, the shell of the transducer 1, is filled with a gel mass flush with the edge for forming a coupling element 5a, on which a separate coupling cushion 5b is applied, which may be exchanged for a coupling cushion with other dimensions in the direction of the sound propagation, in order thus to have the possibility of being able to vary the effective forward path between the irradiation surface 3 and the skin surface of the patient, and thus also the depth of the transducer focus in the body of the patient, when required.

Practical trials have shown that the gel mass selected for use as a coupling medium according to the invention perfectly and better fulfills the set object in comparison to other gel masses used for the same purpose. In any case, it has been shown that extremely low sound energy losses occur, that the gel mass is skin-friendly, has a large UV-resistance and a good shape stability.

We claim:

1. A method for transmitting acoustic waves from a sound source onto a patient body, comprising providing a gel mass coupling medium between the sound source and the patient body, wherein the gel mass comprises a reaction product of polyol components and polyisocyanate components in which the polyol components comprise at least one polyol having a hydroxyl number below 112, wherein the reaction product has an isocyanate number lying in a range of 15 to 59.81, and wherein a product of isocyanate functionality and functionality of the polyol component is at least 6.15.

2. The method according to claim 1, wherein the gel mass further comprises at least one of other polyols and additives.

3. The method according to claim 1, wherein the gel mass further comprises at least one of fillers and additives known from polyurethane chemistry in a total amount of up to about 50 wt % of the total weight of the gel mass.

4. In an apparatus for transmitting acoustic waves from a sound source onto a patient body, wherein a coupling medium is provided between the sound source and the patient body, the improvement comprising the coupling medium being a gel mass comprising a reaction product of polyol components and polyisocyanate components in which the polyol components comprise at least one polyol having a hydroxyl number below 112, wherein the reaction product has an isocyanate number lying in a range of 15 to 59.81, and wherein a product of isocyanate functionality and functionality of the polyol component is at least 6.15.

5. The apparatus according to claim 4, wherein the gel mass further comprises at least one of other polyols and additives.

6. The apparatus according to claim 4, wherein the gel mass further comprises at least one of fillers and additives known from polyurethane chemistry in a total amount of up to about 50 wt % of the total weight of the gel mass.

7. The method according to claim 1, wherein the method comprises acoustic therapy.

8. The method according to claim 3, wherein the acoustic therapy is selected from the group consisting of lithotripsy and hyperthermia.

9. The method according to claim 1, wherein the gel mass comprises a shape stable body.

10. The method according to claim 1, wherein the sound source is an electro-acoustic transducer.

11. The method according to claim 10, wherein the gel mass forms at least one coupling cushion between the transducer and the patient body.

12. The method according to claim 11, wherein the coupling medium comprises at least two coupling cushions arranged in layers.

13. The apparatus according to claim 4, wherein the apparatus is an acoustic therapy apparatus.

14. The apparatus according to claim 13, wherein the acoustic therapy apparatus is selected from the group consisting of lithotripsy apparatus and hyperthermia apparatus.

15. The apparatus according to claim 14, wherein the gel mass comprises a shape stable body.

16. The apparatus according to claim 4, where the sound source is an electro-acoustic transducer.

17. The apparatus according to claim 16, wherein the gel mass forms at least one coupling cushion between the transducer and the patient body.

18. The apparatus according to claim 17, wherein the coupling medium comprises at least two coupling cushions arranged in layers.

* * * * *

UNITED STATES PATENT AND TRADEMARK OFFICE
CERTIFICATE OF CORRECTION

PATENT NO.    : 6,726,904 B2
DATED         : April 27, 2004
INVENTOR(S)   : Werner Krauss et al.

It is certified that error appears in the above-identified patent and that said Letters Patent is hereby corrected as shown below:

<u>Title page,</u>
Item [73], the second Assignee should read -- TechnoGel GmbH & Co. KG. --

Signed and Sealed this

Twentieth Day of July, 2004

JON W. DUDAS
*Acting Director of the United States Patent and Trademark Office*